United States Patent [19]

Rosenberg

[11] Patent Number: 4,610,660
[45] Date of Patent: Sep. 9, 1986

[54] METHOD OF PERFORMING A NEPHROSTOMY PROCEDURE WITH CONNECTOR ASSEMBLY

[75] Inventor: Helmut W. G. Rosenberg, McHenry, Ill.

[73] Assignee: The Kendall Company, Boston, Mass.

[21] Appl. No.: 683,054

[22] Filed: Dec. 18, 1984

[51] Int. Cl.$^4$ ............................................. A61M 25/00
[52] U.S. Cl. ........................................ 604/49; 604/102
[58] Field of Search ................................ 604/99–103; 128/3

[56] References Cited

U.S. PATENT DOCUMENTS

| | | | |
|---|---|---|---|
| 3,144,020 | 8/1964 | Zingale | 128/3 |
| 3,385,301 | 5/1968 | Harautuneian | 604/99 |
| 3,741,217 | 6/1973 | Ciarico | 128/349 |
| 3,805,794 | 4/1974 | Schlesinger | 128/349 R |
| 3,961,632 | 6/1976 | Moossun | 128/347 |
| 4,176,660 | 12/1979 | Mylrea | 128/671 |
| 4,405,314 | 9/1983 | Cope | 604/104 |

OTHER PUBLICATIONS

*Catheters and Accessories,* American Cystoscope Makers, Inc., 1960, p. 15.

Primary Examiner—Dalton L. Truluck
Assistant Examiner—Karen L. Kaechele
Attorney, Agent, or Firm—Powell L. Sprunger

[57] ABSTRACT

A method of performing a nephrostomy procedure comprising the steps of inserting a catheter into a patient's body until a distal portion of the catheter is located in the renal calyces, inflating a sleeve of the catheter in the renal calyces, removing a proximal connector and valve of the catheter, and inserting a sheath of a scope over a shaft of the catheter.

2 Claims, 7 Drawing Figures

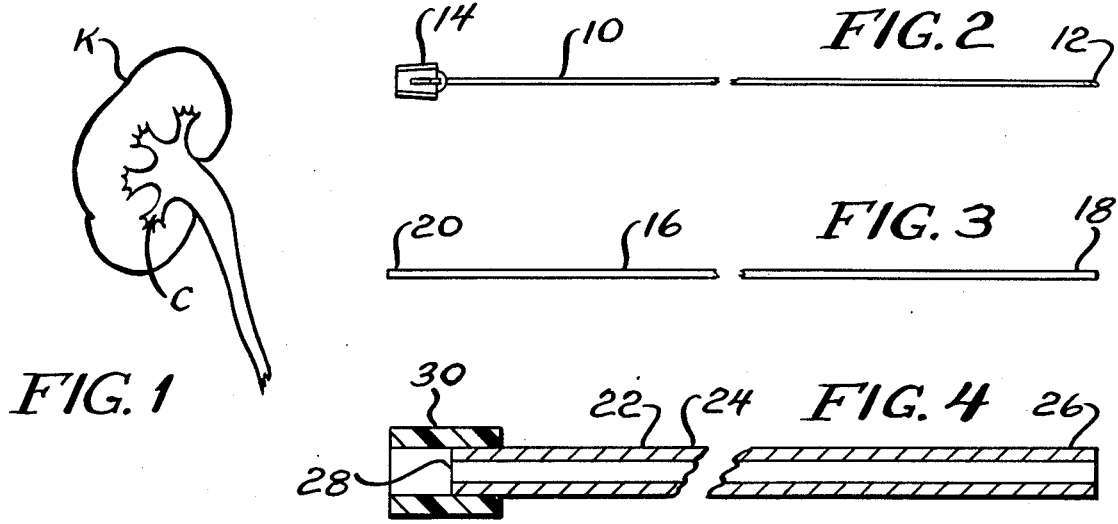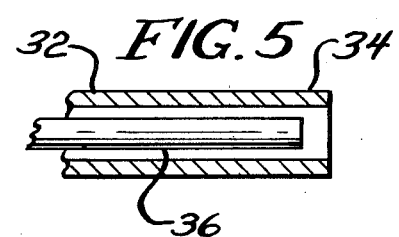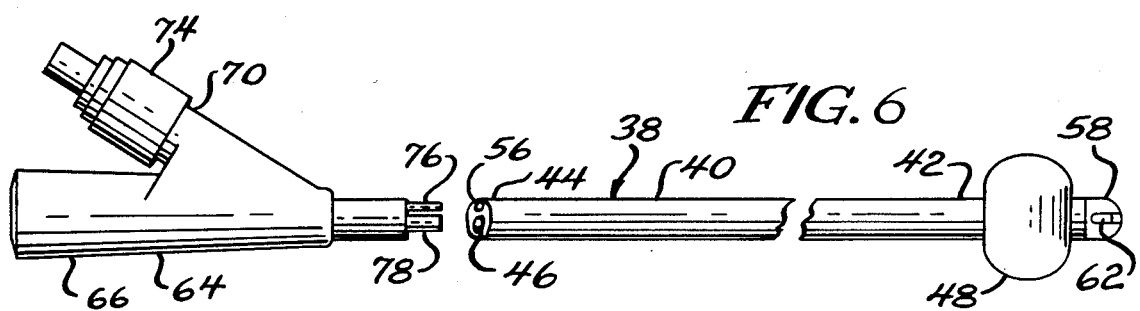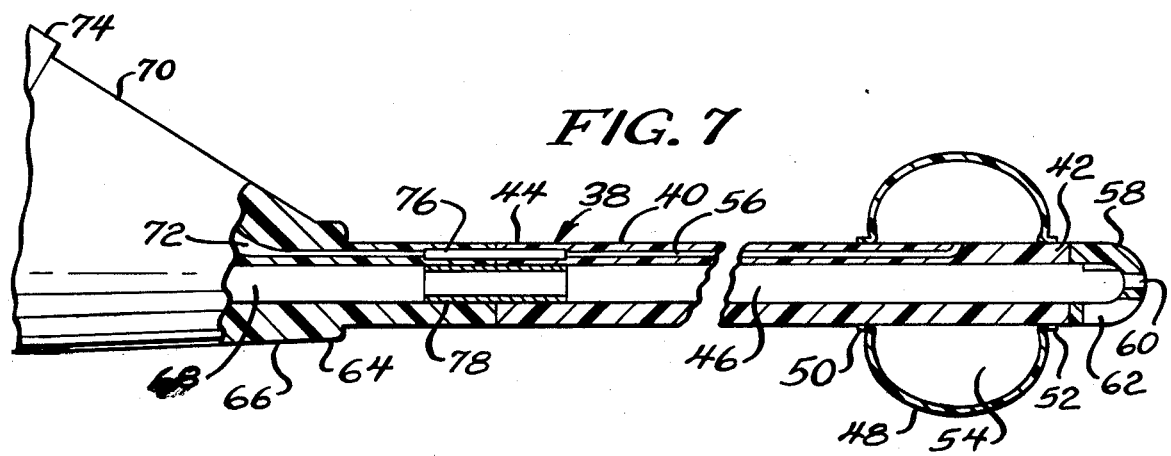

METHOD OF PERFORMING A NEPHROSTOMY PROCEDURE WITH CONNECTOR ASSEMBLY

BACKGROUND OF THE INVENTION

The present invention relates to catheters.

When the ureter or kidney of a patient is obstructed by a stone, it is necessary to stabilize the kidney through drainage because an increase of pressure in the kidney could result in loss of the kidney. Such a procedure is called a nephrostomy procedure. First, a small gauge hollow needle is passed under radiologic vision until a tip of the needle is located in the renal calyces to obtain access to the kidney chamber. With the needle in place, a flexible elongated guide wire is passed through the needle, and the needle is removed with the guide wire in place to establish a path to the kidney. Next, a plurality of dilators are inserted over the guide wire in order to increase the size of the path to the kidney, and the dilators are then removed. In the past, a catheter is then placed over the guide wire, with the catheter having a pig tail which is located in the kidney. Although nephrostomy has been completed in this manner, it is desired to improve the procedure.

SUMMARY OF THE INVENTION

A principal feature of the present invention is the provision of an improved method of performing a nephrostomy procedure.

The method of the present invention comprises the steps of inserting a catheter into a patient's body until a distal portion of the catheter is located in the renal calyces, and inflating a sleeve of the catheter in the renal calyces.

A feature of the invention is the provision of the step of removing a proximal connector and valve of the catheter.

Another feature of the invention is that a sheath of a scope may be inserted over a shaft of the catheter once the connector and valve have been removed.

Further features will become more fully apparent in the following description of the embodiments of this invention and from the appended claims.

DESCRIPTION OF THE DRAWINGS

In the drawings:

FIG. 1 is a diagrammatic view of a kidney of a patient;

FIG. 2 is a fragmentary elevational view of a needle for performing a nephrostomy procedure;

FIG. 3 is a fragmentary elevational view of a guide wire for use in the procedure;

FIG. 4 is a fragmentary elevational view of a stylet for use in the procedure;

FIG. 5 is a fragmentary elevational view of a scope for use in the procedure;

FIG. 6 is a fragmentary elevational view being exploded of a catheter for use in the procedure; and FIG. 7 is a fragmentary sectional view of the catheter of FIG. 6.

DESCRIPTION OF THE PREFERRED EMBODIMENTS

Referring now to FIG. 1, there is shown a kidney K of a patient having a renal calyces C defining a cavity in the kidney K. Referring to FIG. 2, there is shown a hollow needle 10 having a sharp distal tip 12 and a proximal hub 14. Referring to FIG. 3, there is shown an elongated guide wire 16 of flexible material having a distal end 18 and a proximal end 20.

Referring to FIG. 4, there is shown a stylet 22 having an elongated rigid hollow tube 24. The tube 24 has a distal end 26, and a proximal end 28. The stylet 22 has a hollow tubular section 30 secured over the proximal end 28 of the tube 24.

With reference to FIG. 5, there is shown a scope 32 for use during nephrostomy. The scope 32 has an outer elongated hollow sheath 34, and an inner optic telescope 36 removably received within the sheath 34.

A catheter generally designated 38 for use in a method of the present invention is illustrated in FIGS. 6 and 7. The catheter 38 has an elongated elastic shaft 40, with the shaft 40 having a distal end 42, a proximal end 44, and a drainage lumen 46 extending through the shaft 40.

The catheter 38 has an elastic sleeve 48 mounted to the shaft 40 in spaced circumferential zones 50 and 52, such that the sleeve 48 defines a cavity 54 beneath the sleeve 48. As shown, the shaft 40 has an inflation lumen 56 extending through a wall of the shaft 40 and communicating with the cavity 54 beneath the sleeve 48.

The catheter 38 has a formed tip 58 bonded to the distal end 42 of the shaft 40. The tip 58 has a distal opening 60 extending through the tip 58 and communicating with the drainage lumen 46. The tip 58 also has a plurality of drainage eyes 62 located intermediate the opening 60 and a proximal end of the tip 58 and communicating with the drainage lumen 46.

The catheter 38 has a connector assembly 64 which may be removably connected to the proximal end 44 of the shaft 40. The connector assembly 64 has a hollow connector 66 defining a drainage lumen 68. The connector assembly 64 also has a side arm 70 defining an inflation lumen 72. The side arm 70 is attached to a valve 74 of known type which actuates by contact of a tip of a syringe.

The connector assembly 64 has a hollow rigid tubular section 76 received in the inflation lumen 72 and permanently secured to the connector assembly 64. The connector assembly 64 also has a second hollow rigid tubular section 78 received in the drainage lumen 68 and permanently secured to the connector assembly 64. As shown, the connector assembly 64 may be attached to the proximal end 44 of the shaft 40, with the tubular section 76 being received in the inflation lumen 56, and with the tubular section 78 being received in the drainage lumen 46. In this configuration, the tubular section 76 establishes communication between the inflation lumens 56 and 72, and the tubular section 78 establishes communication between the drainage lumens 46 and 68. The tubular sections 76 and 78 are frictionally engaged against an inner surface of the inflation lumen 56 and drainage lumen 46 in order to retain the connector assembly 64 in place against the proximal end 44 of the shaft 40.

In use, the needle 10 is passed under radiologic vision until the tip 12 of the needle 10 is located in the renal calyces C to obtain access to the kidney chamber. With the needle 10 in place, the guide wire 16 is passed through the needle 10, and the needle 10 is removed with the guide wire 16 in place to establish a path to the kidney K. Next, a plurality of dilators are inserted over the guide wire 16 in order to increase the size of the path to the kidney K, and the dilators are then removed.

The stylet 22 is then passed through the drainage lumens 68 and 46 of the catheter 38 until the distal end 26 of the stylet 22 engages against the tip 58. The guide wire 16 is received in the opening 60 and the inside of the stylet 22, and the catheter 38 and stylet 22 are passed over the guide wire 16 with the stylet 22 supplying rigidity to the catheter 38 during passage over the guide wire 16.

The catheter 38 is passed over the guide wire 16 until a distal end portion of the catheter 38 is located in the renal calyces. Next, the tip of a syringe is utilized to actuate the valve 74, and a suitable fluid is pumped through the inflation lumens 72 and 56 into the cavity 54 in order to inflate the sleeve 48 in the renal calyces. The stylet 22 is then removed from the catheter 38, and the connector 66 is attached to an upstream portion of a drainage tube which is connected to a drainage bag, and urine drains through the catheter 38 and drainage tube into the collection bag for retention therein.

When the physician desires to view the inside of the kidney, the scope 32 is utilized in the procedure. First, the connector assembly 64 is removed from the shaft 40 which permits deflation of the sleeve 48. Next, the sheath 34 of the scope 32 is passed over the catheter shaft 40, and the catheter 38 is removed from the sheath 34. Finally, the optic telescope 36 is inserted through the sheath 34 in order to view the inside of the kidney K. During this procedure, the catheter 38 facilitates insertion of the sheath 34, since it is unnecessary to redefine the tract leading to the kidney K.

When viewing of the kidney K has been completed, the telescope 36 is removed from the sheath 34, and the catheter 38 less the connector assembly 64 is inserted through the sheath until the distal portion of the catheter 38 is located in the renal calyces. Next, the sheath 34 is removed from the catheter 38, and the connector assembly 64 is attached to the proximal end 44 of the shaft 40, and the sleeve 48 is again inflated in the renal calyces C through use of a syringe.

According to a method of performing a nephrostomy procedure of the present invention a catheter is inserted into a patient's body until a distal portion of the catheter is located in the renal calyces, a sleeve of the catheter is inflated in the renal calyces, a proximal connector and valve of the catheter are removed, and a sheath of a scope is inserted over a shaft of the catheter.

The foregoing detailed description is given for clearness of understanding only, and no unnecessary limitations should be understood therefrom, as modifications will be obvious to those skilled in the art.

1. A method of performing a nephrostomy procedure comprising the steps of:

establishing a pathway to the renal calyces;

inserting an inflatable sleeve catheter with a proximal connector and an inflation valve a catheter into a patient's body until a distal portion of the catheter is located in the renal calyces;

inflating a sleeve of the catheter in the renal calyces;

removing a proximal connector and valve of the catheter such that the sleeve deflates;

telescopically passing a sheath of a scope over a shaft of said catheter located in the patient's body;

removing the catheter through the sheath; and inserting a telescope of the scope through the sheath.

2. The method of claim 1 including the steps of removing the telescope from the sheath, inserting the catheter through the sheath, removing the sheath over the catheter shaft, attaching the connector and valve to the catheter shaft, and inflating the sleeve in the renal calyces.

* * * * *